(12) United States Patent
Yao et al.

(10) Patent No.: US 11,790,528 B2
(45) Date of Patent: Oct. 17, 2023

(54) PREOPERATIVE SURVIVAL PREDICTION METHOD BASED ON ENHANCED MEDICAL IMAGES AND COMPUTING DEVICE USING THEREOF

(71) Applicant: Ping An Technology (Shenzhen) Co., Ltd., Shenzhen (CN)

(72) Inventors: Jiawen Yao, Bethesda, MD (US); Ling Zhang, Bethesda, MD (US); Le Lu, Bethesda, MD (US)

(73) Assignee: Ping An Technology (Shenzhen) Co., Ltd., Shenzhen (CN)

( * ) Notice: Subject to any disclaimer, the term of this patent is extended or adjusted under 35 U.S.C. 154(b) by 478 days.

(21) Appl. No.: 17/165,369

(22) Filed: Feb. 2, 2021

(65) Prior Publication Data
US 2022/0245810 A1    Aug. 4, 2022

(51) Int. Cl.
| | |
|---|---|
| *G06T 7/00* | (2017.01) |
| *G16H 30/40* | (2018.01) |
| *G06V 10/46* | (2022.01) |
| *G06F 18/213* | (2023.01) |
| *G06F 18/214* | (2023.01) |

(52) U.S. Cl.
CPC .......... *G06T 7/0014* (2013.01); *G06F 18/213* (2023.01); *G06F 18/2148* (2023.01); *G06V 10/462* (2022.01); *G16H 30/40* (2018.01); *G06T 2207/20084* (2013.01); *G06T 2207/30096* (2013.01)

(58) Field of Classification Search
CPC ......... G06T 7/0014; G06T 2207/20084; G06T 2207/30096; G16H 30/40; G06V 10/462; G06F 18/2148; G06F 18/213
See application file for complete search history.

(56) References Cited

U.S. PATENT DOCUMENTS

2019/0019300 A1* 1/2019 Simpson .................. G06T 7/40

OTHER PUBLICATIONS

A. Chaddad, P. Sargos and C. Desrosiers, "Modeling Texture in Deep 3D CNN for Survival Analysis," in IEEE Journal of Biomedical and Health Informatics, vol. 25, No. 7, pp. 2454-2462, Jul. 2021, doi: 10.1109/JBHI.2020.3025901 (Year: 2021).*

(Continued)

*Primary Examiner* — Amandeep Saini
*Assistant Examiner* — Julius Chai
(74) *Attorney, Agent, or Firm* — ScienBiziP, P.C.

(57) ABSTRACT

A preoperative survival prediction method and a computing device applying the method include constructing a data seta according to a plurality of enhanced medical images and a resection margin of each enhanced medical image and obtaining a plurality of training data sets from the constructed data set. For each training data set, multi-task prediction models are trained. A target multi-task prediction model is selected from the plurality, and a resection margin prediction value and a survival risk prediction value are obtained by predicting an enhanced medical image to be measured through the target multi-task prediction model. The multi-task prediction model more effectively captures the changes over time of the tumor in multiple stages, so as to enable a joint prediction of a resection margin prediction value and a survival risk prediction value.

20 Claims, 5 Drawing Sheets

(56) References Cited

OTHER PUBLICATIONS

J. Jaworek-Korjakowska, et al. "Melanoma Thickness Prediction Based on Convolutional Neural Network With VGG-19 Model Transfer Learning," 2019 IEEE/CVF Conference on Computer Vision and Pattern Recognition Workshops (CVPRW), Long Beach, CA, USA, 2019, pp. 2748-2756, doi: 10.1109/CVPR (Year: 2019).*
Hui, Bei, et al. "Identification of pancreaticoduodenectomy resection for pancreatic head adenocarcinoma: a preliminary study of radiomics." Computational and mathematical methods in medicine 2020 (2020) (Year: 2020).*
Wellner, Ulrich F et al. "Mesopancreatic Stromal Clearance Defines Curative Resection of Pancreatic Head Cancer and Can Be Predicted Preoperatively by Radiologic Parameters: A Retrospective Study." Medicine vol. 95,3 (2016): e2529. doi:10.1097/MD.0000000000002529 (Year: 2016).*
Wang, Xiao-Hang, et al. "MRI-based radiomics model for preoperative prediction of 5-year survival in patients with hepatocellular carcinoma." British journal of cancer 122.7 (2020): 978-985. (Year: 2020).*
Eilaghi, Armin et al. "CT texture features are associated with overall survival in pancreatic ductal adenocarcinoma—a quantitative analysis." BMC medical imaging vol. 17,1 38. Jun. 19, 2017, doi:10.1186/s12880-017-0209-5 (Year: 2017).*
Tadayyon, Hadi, et al. "A priori prediction of neoadjuvant chemotherapy response and survival in breast cancer patients using quantitative ultrasound." Scientific reports 7.1 (2017): 45733 (Year: 2017).*
Attiyeh, Marc A., et al. "Survival prediction in pancreatic ductal adenocarcinoma by quantitative computed tomography image analysis." Annals of surgical oncology 25 (2018): 1034-1042. (Year: 2018).*

* cited by examiner

PREOPERATIVE SURVIVAL PREDICTION METHOD BASED ON ENHANCED MEDICAL IMAGES AND COMPUTING DEVICE USING THEREOF

FIELD

The present disclosure relates to a technical field of medical technology, specifically a preoperative survival prediction method based on enhanced medical images and a computing device using thereof.

BACKGROUND

Pancreatic ductal adenocarcinoma (PDAC) is a human cancer, which has an extremely very poor 5-year survival rate of 9%. Surgical sectioning, in combination with neoadjuvant chemotherapy, is the only potentially curative treatment for PDAC patients. However, outcomes vary significantly even among the resected patients of the same stage receiving similar treatments. Accurate preoperative prognosis of PDAC for personalized treatment is thus highly desired.

Previous work adopts image texture analysis for the prediction of survival of PDAC. However, the representation power of hand-crafted features only on the venous phase in computer tomography (CT) may be limited. More recently, cancer outcome prediction models based on deep learning have shown good powers of prediction for lung cancer and gliomas. The success of 3DCNNs contributes not only to the capture of deep features in the 3D gross tumor volume but also in the peritumoral regions. However, such models may not generalize well for PDAC because important predictive information may not exist in the isolated imaging modality/phase.

A solution for preoperative survival prediction is required.

SUMMARY

A first aspect of an embodiment of the present disclosure provides a preoperative survival prediction method based on enhanced medical images. The method includes: constructing a data seta according to a plurality of enhanced medical images and a resection margin of each enhanced medical image, and obtaining a plurality of training data sets from the constructed data set. For each training data set, inputting the training data set into a first network structure and a second network structure for training, extracting first feature maps of the training data sets through the first network structure, and extracting second feature maps of the training data sets through the second network structure. Obtaining joint feature maps by connecting the first feature maps and the second feature maps, obtaining a resection margin risk loss value by calculating a resection margin risk loss function based on the joint feature maps, and obtaining a survival risk loss value by calculating a survival risk loss function based on the joint feature maps Determining whether the resection margin risk loss value and the survival risk loss value meet their respective loss thresholds and when the resection margin risk loss value and the survival risk loss value both meet their respective loss thresholds, stopping the training of the first network structure and the second network structure to obtain a plurality of multi-task prediction models. Selecting a target multi-task prediction model from the plurality of multi-task prediction models and obtaining a resection margin prediction value and a survival risk prediction value by predicting an enhanced medical image to be measured through the target multi-task prediction model.

A second aspect of an embodiment of the present disclosure provides a computing device, which includes at least one processor and a storage device storing one or more programs which when executed by the at least one processor, causes the at least one processor to construct a data seta according to a plurality of enhanced medical images and a resection margin of each enhanced medical image, and obtain a plurality of training data sets from the constructed data set. For each training data set, input the training data set into a first network structure and a second network structure for training, extract first feature maps of the training data sets through the first network structure, and extract second feature maps of the training data sets through the second network structure. Obtain joint feature maps by connecting the first feature maps and the second feature maps, obtain a resection margin risk loss value by calculating a resection margin risk loss function based on the joint feature maps, and obtain a survival risk loss value by calculating a survival risk loss function based on the joint feature maps. Determine whether the resection margin risk loss value and the survival risk loss value meet their respective loss thresholds and when the resection margin risk loss value and the survival risk loss value both meet their respective loss thresholds, stop the training of the first network structure and the second network structure to obtain a plurality of multi-task prediction models. Select a target multi-task prediction model from the plurality of multi-task prediction models and obtain a resection margin prediction value and a survival risk prediction value by predicting an enhanced medical image to be measured through the target multi-task prediction model.

A third aspect of an embodiment of the present disclosure provides a non-transitory storage medium having stored thereon instructions that, when executed by a processor of a computing device, causes the computing device to perform a method for preoperative prediction of survival. The method includes constructing a data set according to a plurality of enhanced medical images and a resection margin of each enhanced medical image, and obtaining a plurality of training data sets from the constructed data set. For each training data set, inputting the training data set into a first network structure and a second network structure for training, extracting first feature maps of the training data sets through the first network structure, and extracting second feature maps of the training data sets through the second network structure. Obtaining joint feature maps by connecting the first feature maps and the second feature maps, and obtaining a resection margin risk loss value by calculating a resection margin risk loss function based on the joint feature maps, and also obtaining a survival risk loss value by calculating a survival risk loss function based on the joint feature maps. Determining whether the resection margin risk loss value and the survival risk loss value meet their respective loss thresholds; when the resection margin risk loss value and the survival risk loss value both meet their respective loss thresholds, stop the training of the first network structure and the second network structure to obtain a plurality of multi-task prediction models. Selecting a target multi-task prediction model from the plurality of multi-task prediction models and obtaining a resection margin prediction value and a survival risk prediction value by predicting an enhanced medical image to be measured through the target multi-task prediction model.

In the embodiments of the present disclosure, by constructing a data seta according to a plurality of enhanced medical images and a resection margin of each enhanced medical image, and obtaining a plurality of training data sets from the constructed data set. For each training data set, a multi-task prediction models is trained. A target multi-task prediction model is selected from the plurality of multi-task prediction models and a resection margin prediction value and a survival risk prediction value are obtained by predicting an enhanced medical image to be measured through the target multi-task prediction model. The multi-task prediction model captures more effectively the time changes of the tumor in multiple stages, so as to make a joint prediction of a resection margin prediction value and a survival risk prediction value.

DETAILED DESCRIPTION

The embodiments of the present disclosure are described with reference to the accompanying drawings. Described embodiments are merely embodiments which are a part of the present disclosure, and do not include every embodiment. All other embodiments obtained by those of ordinary skill in the art based on the embodiments of the present disclosure without creative efforts are within the scope of the claims.

Terms such as "first", "second" and the like in the specification and in the claims of the present disclosure and the above drawings are used to distinguish different objects, and are not intended to describe a specific order. Moreover, the term "include" and any variations of the term are intended to indicate a non-exclusive inclusion. For example, a process, a method, a system, a product, or a device which includes a series of steps or units is not limited to steps or units which are listed, but can include steps or units which are not listed, or can include other steps or units inherent to such processes, methods, products, and equipment.

Figure 1:
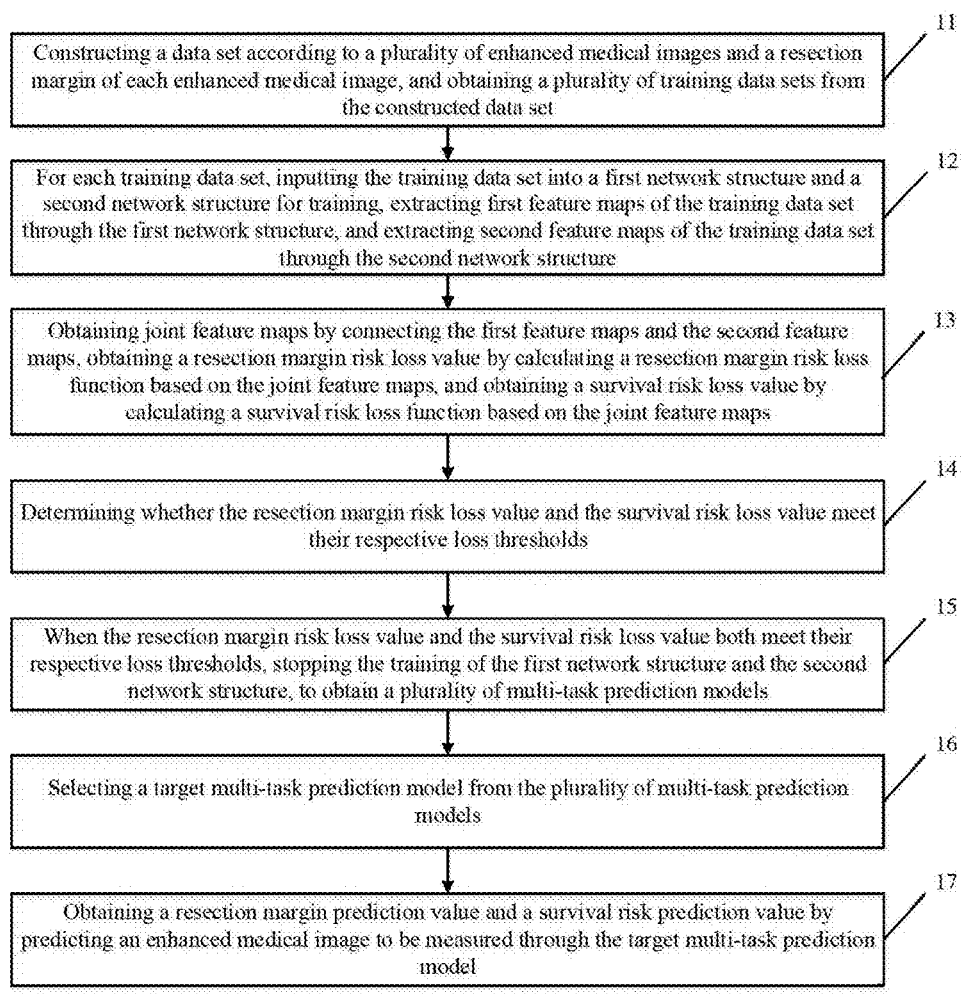
FIG. 1 shows a schematic flow chart of an embodiment of a preoperative survival prediction method based on enhanced medical images according to the present disclosure.

FIG. 1 shows a schematic flow chart of an embodiment of a preoperative survival prediction method based on enhanced medical images according to the present disclosure.

As shown in FIG. 1, the preoperative survival prediction method based on enhanced medical images applicable in a computing device can include the following steps. According to different requirements, the order of the steps in the flow chart may be changed, and some steps may be omitted.

In block 11, constructing a data set according to a plurality of enhanced medical images and a resection margin of each enhanced medical image, and obtaining a plurality of training data sets from the constructed data set.

In some embodiments, a series of medical images are obtained by scanning a patient's body or a part with an image scanning device after intravenous injection of contrast media. Medical images obtained by scanning a patient using an image scanning device after intravenous injection of contrast media are called enhanced medical images. Enhanced medical image corresponding to different phases between a plurality of planes can be considered as one frame in the series of enhanced medical images. That is, the series of enhanced medical images will include a plurality of enhanced medical images. With application of contrast media for clinical purposes, effectiveness of images is enhanced, and accuracy of diagnoses is improved.

The patient may be a patient suffering from any tumor, such as a pancreatic ductal adenocarcinoma, a liver tumor, a lung tumor, a lymphoma tumor, a hepatic hemangioma, or the like. The image scanning device can utilize, for example, a Computer Tomography (CT), a Magnetic Resonance Imaging (MRI), a positron emission tomography (PET), a single photon emission computed tomography (SPECT), an ultrasound scanning, a rotational angiography, and other medical imaging modalities. Correspondingly, the enhanced medical image can be an enhanced CT image, an enhanced MRI image, an enhanced PET image, an enhanced SPECT image, an enhanced ultrasound scan image, and an enhanced rotational angiography image and other enhanced medical imaging modal images.

In order to facilitate understanding of the present disclosure, the following describes an example of enhanced CT images of PDAC patients.

In some embodiments, the method of constructing a data set according to a plurality of enhanced medical images and a resection margin of each enhanced medical image includes: obtaining a plurality of first target images by delineating a first target region in each enhanced medical image corresponding to a first phase; obtaining a plurality of second target images by segmenting a second target region in each enhanced medical image corresponding to a second phase; constructing an array by combining one enhanced medical image and the corresponding first target image, the corresponding second target image, and the corresponding resection margin, the data set including a plurality of the arrays.

Phases shown in the enhanced CT images of the pancreatic ductal adenocarcinoma patient include a non-contrast phase, a pancreatic phase, and a venous phase. The non-contrast phase is before any contrast media is injected into body of the patient. The pancreatic phase (also called arterial phase) is when a contrast media is moved from the heart into the arteries, all structures/organs that get their blood supply from the arteries will show optimal enhancement. In the aorta, a major enhancement can be observed. The venous phase is when the contrast media is in the veins, flowing back to the heart. In the venous phase, the liver parenchyma is enhanced through blood supply by the portal vein and some enhancement of the hepatic veins can be seen. Pancreatic CT scans of 205 patients (with significant PDACs, meaning tumor size=2.5 cm) were undertaken preoperatively during non-contrast, pancreatic, and portal venous phases (i.e., 615 CT volumes). Only 24 out of 205 patients have R1 resection margins, and the imbalance in a resection margin loss is considered.

In this embodiment, the first phase can be the pancreatic phase, and the second phase can be the venous phase. The first target region in each enhanced medical image can be a pancreas region. The second target region in each enhanced medical image can be a tumor region. The first target region can be delineated on the pancreatic phase by a radiologist with 18 years of experience in manual pancreatic imaging. The second target region can be segmented automatically by a nnUNet (no-new-Net) model trained on a public pancreatic cancer dataset with annotations. The nnUNet model is known in prior art, and a process of segmenting the second target region using the nnUNet model is also prior art. The present disclosure will not describe the same in detail herein.

In some embodiments, the array can be prepared for every tumor volume and the array $X_t=\{X_t^{CT}, X_t^{M_T}, X_t^{M_P}\}$, $t \in \{1, 2, 3\}$, respectively represent the non-contrast phase, the venous phase, and the pancreatic phase. $C_T$ represents an enhanced medical image corresponding to the non-contrast phase, $M_T$ represents a second target image (tumor mask) corresponding to the venous phase, and $M_P$ represents a first target image (pancreas mask) corresponding to the pancreatic phase.

In some embodiments, a pre-trained 3D convolutional neural network model can be used to detect a phase of each enhanced medical image in the series of enhanced medical images. The phase of each enhanced medical image in the series of enhanced medical images is re-marked by the pre-trained 3D convolutional neural network model to obtain an accurate phase, thereby enabling effective management of the enhanced medical images. Each of the enhanced medical images corresponds to one phase, and different enhanced medical images may correspond to different phases.

In some embodiments, in order to remove noise from the each enhanced medical image, the method also includes, before constructing of the data set, defining a first threshold value and a second threshold value greater than the first threshold value; comparing each pixel value in the enhanced medical image with the first threshold value and comparing each pixel value in the enhanced medical image with the second threshold value; updating a pixel value according to the first threshold value, and when the pixel value in the enhanced medical image is smaller than the first threshold value; updating a pixel value according to the second threshold value. When the pixel value in the enhanced medical image is greater than the second threshold value, keeping a pixel value unchanged; and when the pixel value in the enhanced medical image is greater than the first threshold but less than the second threshold; updating the enhanced medical image according to the updated pixel value.

In some embodiments, after updating each enhanced medical image, the method also includes: obtaining a plurality of resampled enhanced medical images by resampling each enhanced medical image into an isotropic enhanced medical image; and enhancing the plurality of resampled enhanced medical images.

All the enhanced medical images can be resampled to an isotropic 1 mm^3 resolution. In order to expand the constructed data set, all of the resampled enhanced medical images in the plurality can be enhanced. Training a multi-task prediction model based on the expanded data set can improve a generalization ability of the multi-task prediction model.

In some embodiments, the method of enhancing the plurality of resampled enhanced medical images includes: rotating the plurality of resampled enhanced medical images according to a pre-rotation angle; or randomly zooming the plurality of resampled enhanced medical images.

For example, the pre-rotation angle can be 90°. Rotating the volume of tumors axially around the tumor center with the step size of 90° to get the corresponding 3D CT image patches and their mirrored patches. A multi-phase sequence of image sub volumes of 64×64×64 centered at the tumor 3D centroid are cropped to cover the entire tumor and its surrounding pancreas regions.

In block 12, for each training data set, inputting the training data set into a first network structure and a second network structure for training, extracting first feature maps of the training data set through the first network structure, and extracting second feature maps of the training data set through the second network structure.

Figure 2:
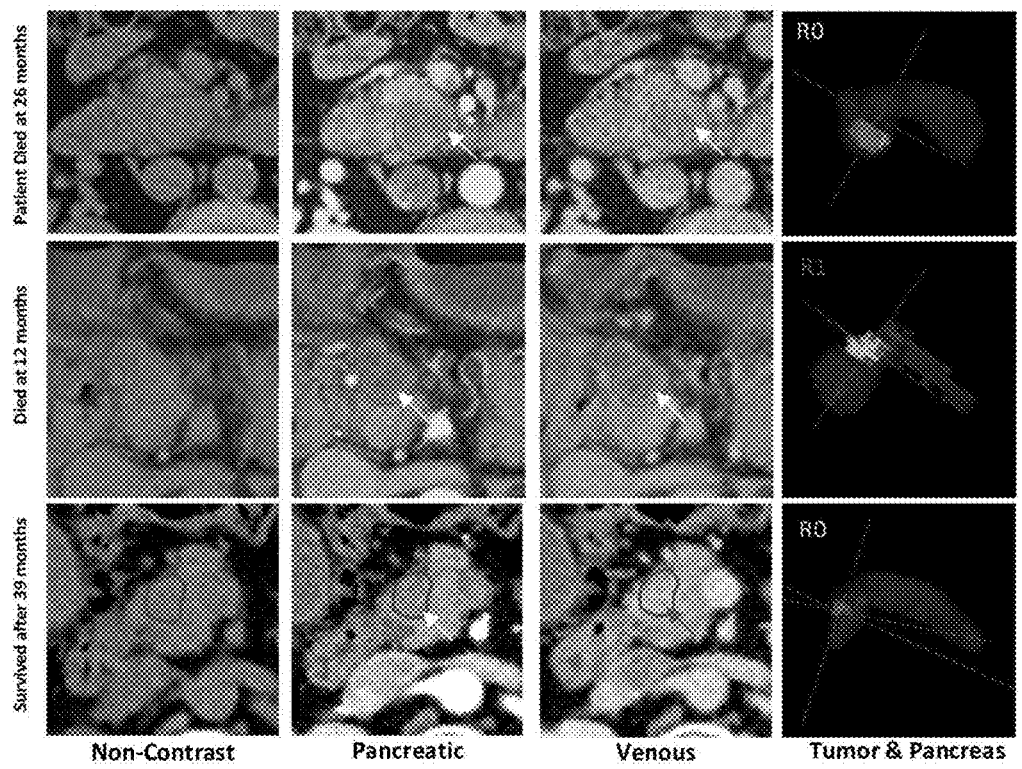
FIG. 2 shows a schematic diagram of an example of the multi-phase (dynamic) CE-CT images and pancreatic ductal adenocarcinoma (PDAC) tumor enhancement patterns according to the present disclosure.

The preoperative multi-phase CE-CT pancreatic imaging used in the present disclosure are the result of being scanned at three time points for PDACs located at the pancreas head and uncinate. After the non-contrast phase, average imaging time delays are 40-50 seconds for the pancreatic phase and 65-70 seconds for the portal venous phase. FIG. 2 shows three examples illustrating different tumor attenuations and resection margins of PDAC patients. Tumor attenuation in specific CT phases is very important characteristic to identify and detect the tumor. Each row in FIG. 2 represents one PDAC patient, and black boundaries represent the tumor annotations. The white arrow indicates a typical hypo-attenuating tumor, while gray arrow shows an iso-attenuating tumor. In previous studies, Kim et al. stated that visually iso-attenuating PDACs are associated with better survival rates after surgery, as opposed to typical hypo-attenuating. Hypo-attenuating mass can be clearly observed in both pancreatic and venous phases of the first and second patients, indicating low stromal fractions (worse clinical outcomes). For the third patient, even though tumor hypo-attenuating is observed in pancreatic phase, it then reflects iso- or even hyper-attenuating in the venous phase compared with its adjacent pancreas regions, indicating high stromal fractions (better survival). Tumor enhancement changes across phases is a very useful marker to reflect tumor internal variations and can benefit prognosis.

Besides tumor attenuation, another very important factor is the resection margin status indicating whether cancer cells are present within 1 mm of all resection margins. More specifically, the resection margin status is characterized as R0 when no evidence of malignant glands is identified at any of the resection margins. R1 resections have malignant glands infiltrating at least one of the resection margins on the permanent section and are usually associated with poor overall survival. From the FIG. 2, both tumors from the first and second patient display hypo-attenuating appearances, but clearly the second tumor has infiltrated out of the pancreas shown in tumor and pancreas masks. The pathological evidence indicates that the second patient has the PDAC with R1 resections, and a follow-up study shows this patient has worse outcome than the first patient. Radiological observations about tumor attenuation and surgical margins status from CE-CT imaging motivate the development of a preoperative PDAC survival model.

Figure 3:
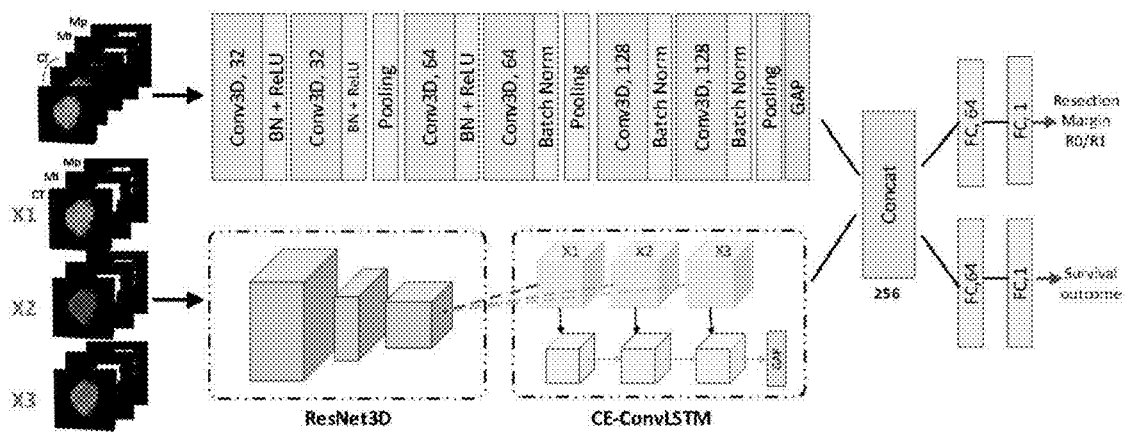
FIG. 3 shows a schematic structural diagram of a network architecture of a multi-task prediction model according to the present disclosure.

Referring to FIG. 3, a schematic structural diagram of a network architecture of a multi-task prediction model according to the present disclosure is shown. Time points 1, 2, 3 are used to represent non-contrast. The network architecture of a multi-task prediction model has two branches: a first branch and a second branch, the first branch used for predicting a resection margin prediction value and the second branch used for predicting a survival risk prediction value.

The first branch uses one 3D-CNN model with six convolutional layers equipped with Batch Normalization and ReLu. Input of the first branch is a concatenation of CT volumes at different time points and the corresponding first and second images: e.g., $X \in R^{5 \times 64^3}$. This branch will try to learn the CT intensity attenuation variations and the relationships between tumor and surrounding pancreas regions, which help to classify the tumor into different resection statuses. Note that R0/R1 can only be obtained after the surgery and pathology. But the multi-task prediction model can be applied preoperatively in real scenarios to offer appropriate advice regarding surgical decisions to PDAC patients.

The second branch uses CT volumes at each phase (each phase is CT-$M_T$-$M_P$ three-channel input, $X_t \in R^{3 \times 64^3}$). An aim of the second branch is to capture the tumor attenuation patterns across phases. Tumor attenuation usually means the contrast differences between the tumor and its surrounding pancreas regions so both the tumor and pancreas masks are introduced into input volumes. The core part of this branch is a recurrence module that allows the network to retain what it has seen and to update the memory when it sees a new phase image. A naive approach is to use a vanilla LSTM or ConvLSTM network. Conventional ConvLSTM is capable of modeling 2D spatio-temporal image sequences by explicitly encoding the 2D spatial structures into the temporal domain. Contrast-Enhanced 3D Convolutional LSTM (CE-ConvLSTM) network can be used to capture the temporally enhanced patterns from CE-CT sequences. CE-ConvLSTM can model 4D spatio-temporal CE-CT sequences by explicitly encoding their 3D spatial structures into the temporal domain. The main equations of ConvLSTM are as follows:

$$f_t = \sigma(W_f^X * X_t + W_f^H * H_{t-1} + b_f),$$
$$i_t = \sigma(W_i^X * X_t + W_i^H * H_{t-1} + b_i),$$
$$o_t = \sigma(W_o^X * X_t + W_o^H * H_{t-1} + b_o),$$
$$C_t = f_t \odot C_{t-1} + i_t \odot \tanh(W_C^X * X_t + W_C^H * H_{t-1} + b_C),$$
$$H_t = o_t \odot \tanh(C_t).$$

where $X_t$ is the CE-CT sequences at time t, * denotes the convolution operation, and $\odot$ denotes the Hadamard product. All the gates f, i, o, memory cell C, and hidden state H are 4D tensors. 3×3×3 convolutional kernel and 128 can be used as the channel dimension of hidden states for the LSTM unit. 3D-ResNet18 can be used as the encoder to encode each three-channel input to the lower-dimensional feature maps for CE-ConvLSTM.

In some embodiments, the cropped regions with random shifts can be randomly selected for each iteration during the training process. This data augmentation can improve the network's ability to locate the desired translational invariants. The batch sizes can be 8. The maximum iteration is set to be 500 epochs.

In block 13, obtaining joint feature maps by connecting the first feature maps and the second feature maps, obtaining a resection margin risk loss value by calculating a resection margin risk loss function based on the joint feature maps, and obtaining a survival risk loss value by calculating a survival risk loss function based on the joint feature maps.

In some embodiments, the resection margin risk loss function can be a binary cross-entropy loss function, and the survival risk loss function can be $L(y_i) = \Sigma_i \delta_i(-y_i + \log \Sigma_{j:t_j \geq t_i} \exp(y_j))$, where j is from the set which has survival time equal to or larger than $t_i$ ($t_j \geq t_i$).

After the concatenation of the first feature maps and the second feature maps from both tasks, the channel number of this common representation is 256. Then two separate fully-connected networks will use the common representation for each prediction task. In the training phase, labels of the resection status and patient overall survival information (OS time and censoring status) are known for each input of CE-CT sequence. The weighted binary cross-entropy (BCE) loss is applied to the resection margin prediction task, while the negative log partial likelihood is used to predict the survival outcomes of a certain patient.

In block 14, determining whether the resection margin risk loss value and the survival risk loss value meet their respective loss thresholds.

A first risk loss threshold and a second risk loss threshold can be preset. The first risk loss threshold corresponds to the resection margin risk loss value. The second risk loss threshold corresponds to the survival risk loss value. When the resection margin risk loss value is less than or equal to the first risk loss threshold, it can be determined that the resection margin risk loss value meets the loss threshold. When the resection margin risk loss value is less than or equal to the second risk loss threshold, it can be determined that the resection margin risk loss value meets the loss threshold.

In block 15, when the resection margin risk loss value and the survival risk loss value both meet their respective loss thresholds, stopping the training of the first network structure and the second network structure, to obtain a plurality of multi-task prediction models.

when both the resection margin risk loss value and the survival risk loss value fail to meet their respective loss thresholds, a plurality of training data sets is reacquired from the constructed data set, a plurality of multi-task prediction models being retained.

In block 16, selecting a target multi-task prediction model from the plurality of multi-task prediction models.

However many training data sets there are, there is a one-to-one correspondence between training data sets and multi-task prediction models.

In some embodiments, the method of selecting a target multi-task prediction model from the plurality of multi-task prediction models includes: obtaining a plurality of testing data sets from the constructed data set, each testing data set corresponding to each training data set; obtaining a plurality of testing values by using each testing data set to test the multi-task prediction model; determining a largest testing value among the plurality of testing values; and determining a multi-task prediction model corresponding to the largest testing value as the target multi-task prediction model.

A plurality of arrays are randomly obtained from the constructed data set each time to construct a training data set, and the remaining arrays in the data set can be used to construct a test data set. One test set can be used to test the corresponding multi-task prediction model to obtain the predicted value. The prediction value is used to indicate a prediction performance of the multi-task prediction model. The larger the prediction value, the better the prediction performance of the multi-task prediction model; otherwise, the smaller the prediction value, the worse the prediction performance of the multi-task prediction model. A target multi-task prediction model can be selected from the plurality of multi-task prediction models according to the testing values.

In some embodiments, the method of obtaining a plurality of testing values by using each testing data set to test the corresponding multi-task prediction model includes: calculating a mean value and a variance value of each training data set; standardizing each testing data set according to the mean value and the variance value of the corresponding testing data set; and obtaining the plurality of testing values by using each standardized testing data set to test the corresponding multi-task prediction model. By normalizing each enhanced medical image, a training efficiency of a joint learning model can be improved.

In block 17, obtaining a resection margin prediction value and a survival risk prediction value by predicting an enhanced medical image to be measured through the target multi-task prediction model.

The enhanced medical image to be measured can be an enhanced CT image acquired by using the Computed Tomography to scan PDAC patients preparing for surgery.

Figure 4A:
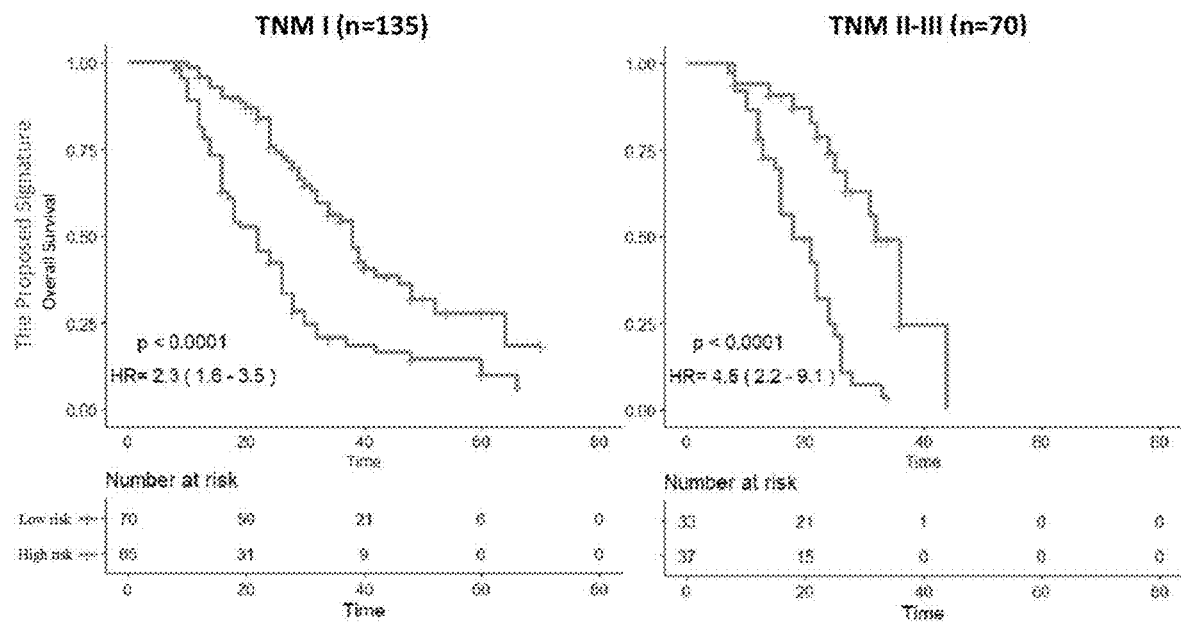
FIG. 4 shows a schematic structural diagram of an embodiment of a risk stratification result according to the present disclosure.
Figure 4A:
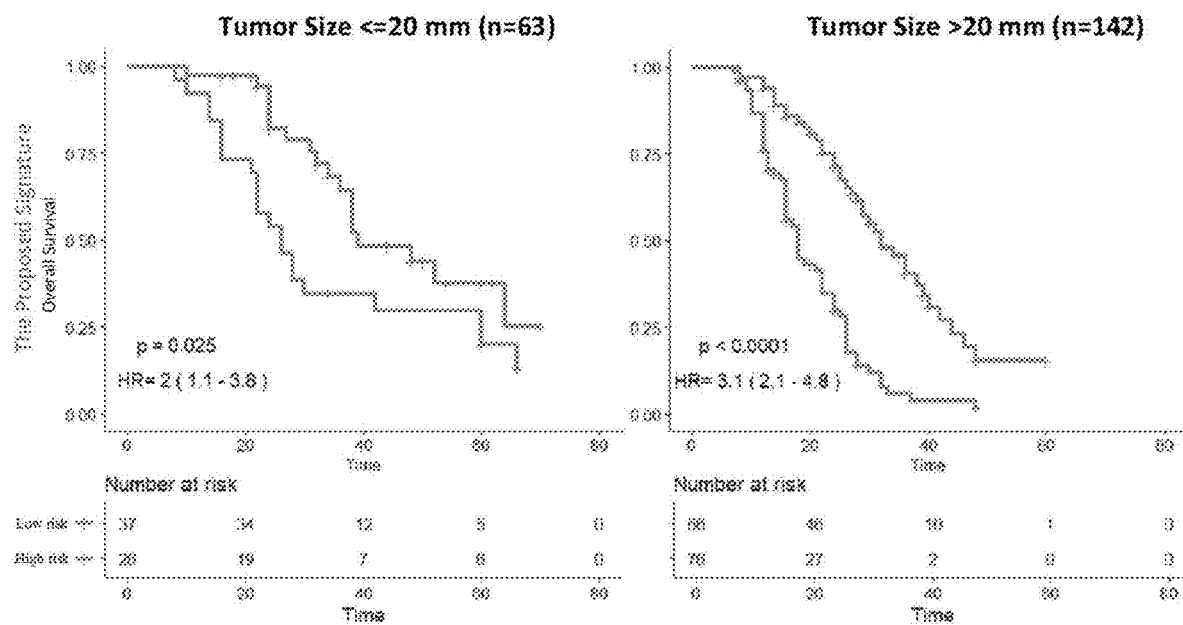
Figure 4B:
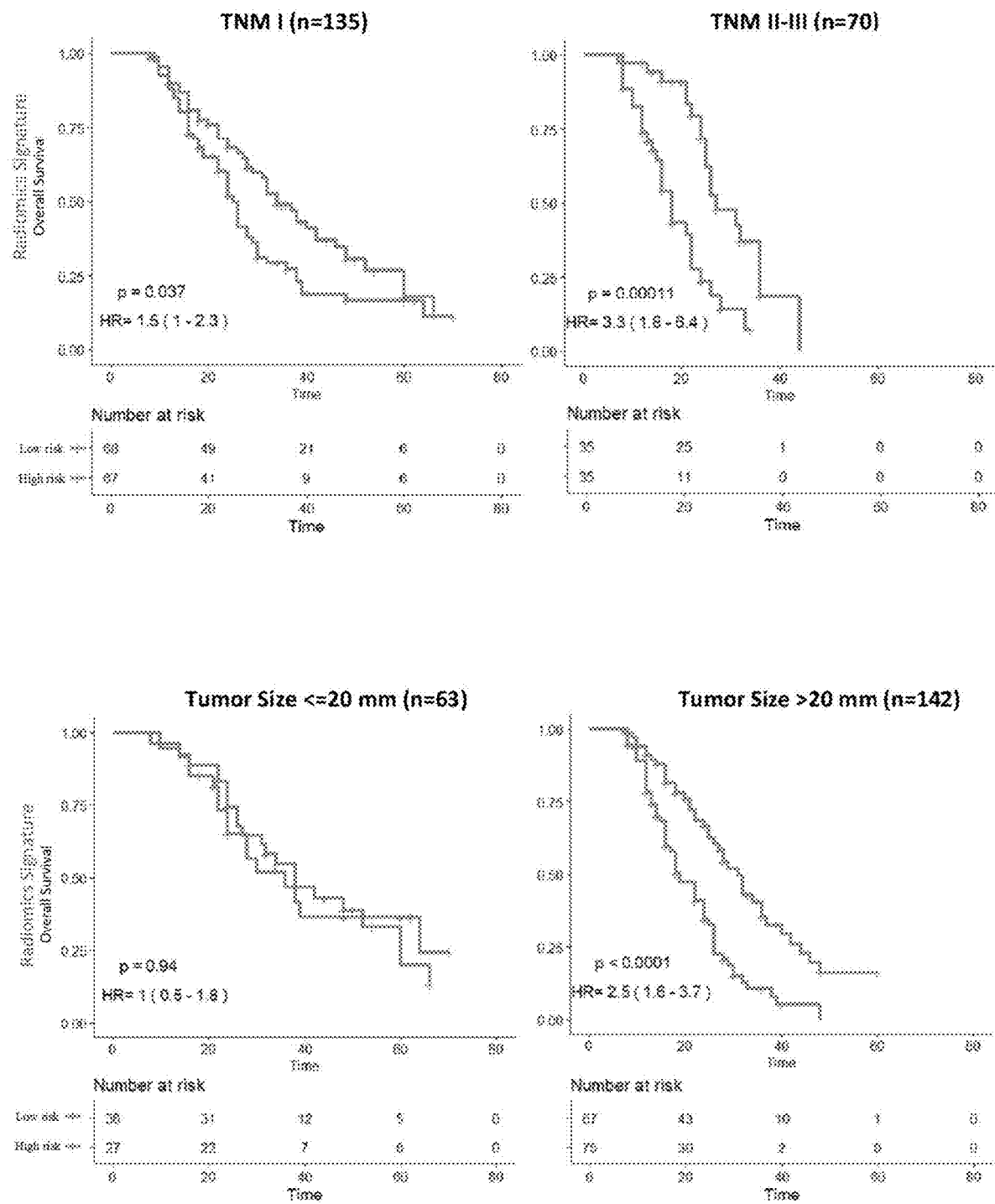

To demonstrate the added value of the proposed signature to the current staging system, Kaplan-Meier survival curves are plotted, as in FIG. 4, for patients with further stratification by the signature after grouping by TNM and Tumor sizes respectively, these being two well-established stratification criteria. The cut-off for radiomics signature is the median score of each signature. Two subgroups of patients are studied: 1) patients divided by TNM staging I vs. II-III, and 2) patients divided by the primary PDAC tumor size≤20 mm vs. >20 mm. It is shown that the proposed signature remains the most significant log-rank test outcome in the subgroup of patients, while the radiomics signature does not reach the statistical significance within the patient subpopulation of PDAC tumor≤20 mm. Results shown in FIG. 3 demonstrate that after using the current clinicopathologic TNM staging system or tumor size, the proposed multi-phase CT imaging-based signature can indeed further provide the risk stratification with significant evidence. This novel deep signature can be combined with the established clinicopathological criteria to refine the risk stratification and guide the individualized treatment of PDAC patients.

The enhanced medical images processing device according to the present disclosure proposes a multi-task prediction model including a novel 3D Contrast-Enhanced Convolutional Long Short-Term Memory (CE-ConvLSTM) network to learn the enhancement dynamics of tumor attenuation from multi-phase CE-CT images. The multi-task prediction model can capture the tumor's temporal changes across several phases more effectively than the early fusion of input images. Furthermore, to allow the tumor resection margin information to contribute to the survival prediction preoperatively, the multi-task prediction model can be used to conduct a joint prediction of a resection margin prediction value and a survival risk prediction value. The joint learning of tumor significance and tumor attenuation in a multi-task setting can benefit both tasks and derive more effective/comprehensive prognosis-related deep image features. Extensive experimental results verify the effectiveness of the presented framework. The signature built from the proposed model remains strong in multivariable analysis adjusting for establishing clinical predictors and can be combined with the established criteria for risk stratification and management of PDAC patients.

Figure 5:
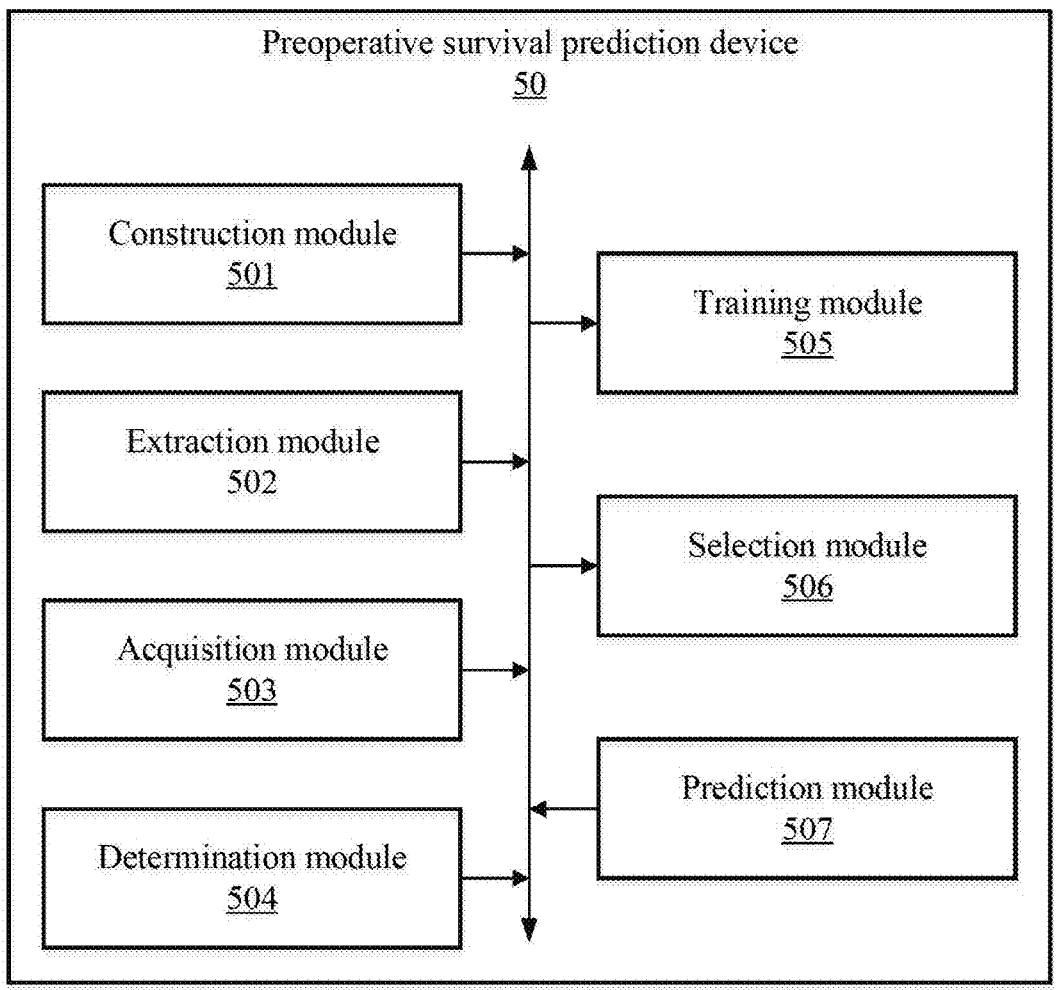
FIG. 5 shows a schematic structural diagram of an embodiment of a preoperative survival prediction device based on enhanced medical images according to the present disclosure.

FIG. 5 shows a schematic structural diagram of an embodiment of a preoperative survival prediction device based on enhanced medical images according to the present disclosure.

In some embodiments, the preoperative survival prediction device 50 can include a plurality of function modules consisting of program code segments. The program code of each program code segments in the device for the preoperative survival prediction device 50 may be stored in a memory of a computing device and executed by the at least one processor to perform (described in detail in FIG. 1) a function of preoperative survival prediction based on enhanced medical images.

In an embodiment, the preoperative survival prediction device 50 can be divided into a plurality of functional modules, according to the performed functions. The functional module can include: a construction module 501, an extraction module 502, an acquisition module 503, a determination module 504, a training module 505, a selection module 506, and a prediction module 507. A module as referred to in the present disclosure refers to a series of computer program segments that can be executed by at least one processor and that are capable of performing fixed functions, which are stored in a memory. In this embodiment, the functions of each module will be detailed in the following embodiments.

The construction module 501 is configured to construct a data set according to a plurality of enhanced medical images and a resection margin of each enhanced medical image, and obtain a plurality of training data sets from the constructed data set.

In some embodiments, a series of medical images are obtained by scanning a patient's body or a part with an image scanning device after intravenous injection of contrast media. Medical images obtained by scanning a patient using an image scanning device after intravenous injection of contrast media are called enhanced medical images. Enhanced medical image corresponding to different phases between a plurality of planes can be considered as one frame in the series of enhanced medical images. That is, the series of enhanced medical images will include a plurality of enhanced medical images. With application of contrast media for clinical purposes, effectiveness of images is enhanced, and accuracy of diagnoses is improved.

The patient may be a patient suffering from any tumor, such as a pancreatic ductal adenocarcinoma, a liver tumor, a lung tumor, a lymphoma tumor, a hepatic hemangioma, or the like. The image scanning device can utilize, for example, a Computer Tomography (CT), a Magnetic Resonance Imaging (MRI), a positron emission tomography (PET), a single photon emission computed tomography (SPECT), an ultrasound scanning, a rotational angiography, and other medical imaging modalities. Correspondingly, the enhanced medical image can be an enhanced. CT image, an enhanced MRI image, an enhanced PET image, an enhanced SPECT image, an enhanced ultrasound scan image, and an enhanced rotational angiography image and other enhanced medical imaging modal images.

In order to facilitate understanding of the present disclosure, the following describes an example of enhanced CT images of PDAC patients.

In some embodiments, the construction module 501 constructing a data set according to a plurality of enhanced medical images and a resection margin of each enhanced medical image includes: obtaining a plurality of first target images by delineating a first target region in each enhanced medical image corresponding to a first phase; obtaining a plurality of second target images by segmenting a second target region in each enhanced medical image corresponding to a second phase; constructing an array by combining one enhanced medical image and the corresponding first target image, and the corresponding second target image, and the corresponding resection margin, the data set including a plurality of arrays.

Phases shown in the enhanced CT images of the pancreatic ductal adenocarcinoma patient include a non-contrast phase, a pancreatic phase, and a venous phase. The non-contrast phase is before any contrast media is injected into body of the patient. The pancreatic phase (also called arterial phase) is when a contrast media is moved from the heart into the arteries, all structures/organs that get their blood supply from the arteries will show optimal enhancement. In the aorta, a major enhancement can be observed. The venous phase is when the contrast media is in the veins, flowing back to the heart. In the venous phase, the liver parenchyma is enhanced through blood supply by the portal vein and some enhancement of the hepatic veins can be seen. Pancreatic CT scans of 205 patients (with significant PDACs, meaning tumor size=2.5 cm) were undertaken preoperatively during non-contrast, pancreatic, and portal venous phases (i.e., 615 CT volumes). Only 24 out of 205 patients have R1 resection margins, and the imbalance in a resection margin loss is considered.

In this embodiment, the first phase can be the pancreatic phase, and the second phase can be the venous phase. The first target region in each enhanced medical image can be a pancreas region. The second target region in each enhanced medical image can be a tumor region. The first target region can be delineated on the pancreatic phase by a radiologist with 18 years of experience in manual pancreatic imaging. The second target region can be segmented automatically by a nnUNet (no-new-Net) model trained on a public pancreatic cancer dataset with annotations. The nnUNet model is known in prior art, and a process of segmenting the second target region using the nnUNet model is also prior art. The present disclosure will not describe the same in detail herein.

In some embodiments, the array can be prepared for every tumor volume and the array $X_t = \{X_t^{CT}, X_t^{M_T}, X_t^{M_P}\}$, $t \in \{1, 2, 3\}$, respectively represent the non-contrast phase, the venous phase, and the pancreatic phase. $C_T$ represents an enhanced medical image corresponding to the non-contrast phase, $M_T$ represents a second target image (tumor mask) corresponding to the venous phase, and $M_P$ represents a first target image (pancreas mask) corresponding to the pancreatic phase.

In some embodiments, a pre-trained 3D convolutional neural network model can be used, to detect a phase of each enhanced medical image in the series of enhanced medical images. The phase of each enhanced medical image in the series of enhanced medical images is re-marked by the pre-trained 3D convolutional neural network model to obtain an accurate phase, thereby enabling effective management of the enhanced medical images. Each of the enhanced medical images corresponds to one phase, and different enhanced medical images may correspond to different phases.

In some embodiments, in order to remove noise from the each enhanced medical image, before constructing the data set, the device 50 also including: define a first threshold value and a second threshold value greater than the first threshold value; compare each pixel value in the enhanced medical image with the first threshold value and comparing each pixel value in the enhanced medical image with the second threshold value; update a pixel value according to the first threshold value, when the pixel value in the enhanced medical image is smaller than the first threshold value; update a pixel value according to the second threshold value, when the pixel value in the enhanced medical image is greater than the second threshold value; keep a pixel value unchanged, when the pixel value in the enhanced medical image is greater than the first threshold but less than the second threshold; update the enhanced medical image according to the updated pixel value.

In some embodiments, a plurality of resampled enhanced medical images can be obtained by resampling each enhanced medical image into an isotropic enhanced medical image after updating each enhanced medical image; and the plurality of resampled enhanced medical images can be enhanced.

All the enhanced medical images can be resampled to an isotropic 1 mm^3 resolution. In order to expand the constructed data set, all of the resampled enhanced medical images in the plurality can be enhanced. Training a multi-task prediction model based on the expanded data set improves a generalization ability of the multi-task prediction model.

In some embodiments, by rotating the plurality of resampled enhanced medical images according to a pre-rotation angle; or randomly zooming the plurality of resampled enhanced medical images, the plurality of resampled enhanced medical images can be enhanced.

For example, the pre-rotation angle can be 90°. Rotating the volume of tumors axially around the tumor center with the step size of 90° to get the corresponding 3D CT image patches and their mirrored patches. A multi-phase sequence of image sub volumes of 64×64×64 centered at the tumor 3D centroid are cropped to cover the entire tumor and its surrounding pancreas regions.

The extraction module 502 is configured to, for each training data set, input the training data set into a first network structure and a second network structure for training, extract first feature maps of the training data set through the first network structure, and extract second feature maps of the training data set through the second network structure.

The preoperative multi-phase CE-CT pancreatic imaging used in the present disclosure are the result of being scanned at three time points for PDACs located at the pancreas head and uncinate. After the non-contrast phase, average imaging time delays are 40-50 seconds for the pancreatic phase and 65-70 seconds for the portal venous phase. FIG. 2 shows three examples illustrating different tumor attenuations and resection margins of PDAC patients. Tumor attenuation in specific CT phases is very important characteristic to identify and detect the tumor. Each row in FIG. 2 represents one PDAC patient, and black boundaries represent the tumor annotations. The white arrow indicates a typical hypo-attenuating tumor, while gray arrow shows an iso-attenuating tumor. In previous studies, Kim et al. stated that visually iso-attenuating PDACs are associated with better survival rates after surgery, as opposed to typical hypo-attenuating. Hypo-attenuating mass can be clearly observed in both pancreatic and venous phases of the first and second patients, indicating low stromal fractions (worse clinical outcomes). For the third patient, even though tumor hypo-attenuating is observed in pancreatic phase, it then reflects iso- or even hyper-attenuating in the venous phase compared with its adjacent pancreas regions, indicating high stromal fractions (better survival). Tumor enhancement changes across phases is a very useful marker to reflect tumor internal variations and can benefit prognosis.

Besides tumor attenuation, another very important factor is the resection margin status indicating whether cancer cells are present within 1 mm of all resection margins. More specifically, the resection margin status is characterized as R0 when no evidence of malignant glands is identified at any of the resection margins. R1 resections have malignant glands infiltrating at least one of the resection margins on the permanent section and are usually associated with poor overall survival. From the FIG. 2, both tumors from the first and second patient display hypo-attenuating appearances, but clearly the second tumor has infiltrated out of the pancreas shown in tumor and pancreas masks. The pathological evidence indicates that the second patient has the PDAC with R1 resections, and a follow-up study shows this patient has worse outcome than the first patient. Radiological observations about tumor attenuation and surgical margins status from CE-CT imaging motivate the development of a preoperative PDAC survival model.

Referring to FIG. 3, a schematic structural diagram of a network architecture of a multi-task prediction model according to the present disclosure is shown. Time points 1, 2, 3 are used to represent non-contrast. The network architecture of a multi-task prediction model has two branches: a first branch and a second branch, the first branch used for predicting a resection margin prediction value and the second branch used for predicting a survival risk prediction value.

The first branch uses one 3D-CNN model with six convolutional layers equipped with Batch Normalization and ReLu. Input of the first branch is a concatenation of CT volumes at different time points and the corresponding first and second images: e.g., $X \in R^{5 \times 64^3}$. This branch will try to learn the CT intensity attenuation variations and the relationships between tumor and surrounding pancreas regions, which help to classify the tumor into different resection statuses. Note that R0/R1 can only be obtained after the surgery and pathology. But the multi-task prediction model can be applied preoperatively in real scenarios to offer appropriate advice regarding surgical decisions to PDAC patients.

The second branch uses CT volumes at each phase (each phase is CT-$M_T$-$M_p$ three-channel input, $X_t \in R^{3 \times 64^3}$). An aim of the second branch is to capture the tumor attenuation patterns across phases. Tumor attenuation usually means the contrast differences between the tumor and its surrounding pancreas regions so both the tumor and pancreas masks are introduced into input volumes. The core part of this branch is a recurrence module that allows the network to retain what it has seen and to update the memory when it sees a new phase image. A naive approach is to use a vanilla LSTM or ConvLSTM network. Conventional ConvLSTM is capable of modeling 2D spatio-temporal image sequences by explicitly encoding the 2D spatial structures into the temporal domain. Contrast-Enhanced 3D Convolutional LSTM (CE-ConvLSTM) network can be used to capture the temporally enhanced patterns from CE-CT sequences. CE-ConvLSTM can model 4D spatio-temporal CE-CT sequences by explicitly encoding their 3D spatial structures into the temporal domain. The main equations of ConvLSTM are as follows:

$$f_t = \sigma(W_f^X * X_t + W_f^H * H_{t-1} + b_f),$$

$$i_t = \sigma(W_i^X * X_t + W_i^H * H_{t-1} + b_i),$$

$$o_t = \sigma(W_o^X * X_t + W_o^H * H_{t-1} + b_o),$$

$$C_t = f_t \odot C_{t-1} + i_t \odot \tanh(W_C^X * X_t + W_C^H * H_{t-1} + b_C),$$

$$H_t = o_t \odot \tanh(C_t).$$

where $X_t$ is the CE-CT sequences at time t, * denotes the convolution operation, and $\odot$ denotes the Hadamard product. All the gates f, i, o, memory cell C, and hidden state H are 4D tensors. 3×3×3 convolutional kernel and 128 can be used as the channel dimension of hidden states for the LSTM unit. 3D-ResNet18 can be used as the encoder to encode each three-channel input to the lower-dimensional feature maps for CE-ConvLSTM.

In some embodiments, the cropped regions with random shifts can be randomly selected for each iteration during the training process. This data augmentation can improve the network's ability to locate the desired translational invariants. The batch sizes can be 8. The maximum iteration is set to be 500 epochs.

The acquisition module 503 is configured to obtain joint feature maps by connecting the first feature maps and the second feature maps, obtain a resection margin risk loss value by calculating a resection margin risk loss function based on the joint feature maps, and obtain a survival risk loss value by calculating a survival risk loss function based on the joint feature maps.

In some embodiments, the resection margin risk loss function can be a binary cross-entropy loss function, and the survival risk loss function can be $L(y_i) = \Sigma_i \delta_i (-y_i + \log \Sigma_{j:t_j \geq t_i} \exp(y_j))$, where j is from the set which has survival time equal to or larger than $t_i$ ($t_j \geq t_i$).

After the concatenation of the first feature maps and the second feature maps from both tasks, the channel number of this common representation is 256. Then two separate fully-connected networks will use the common representation for each prediction task. In the training phase, labels of the resection status and patient overall survival information (OS time and censoring status) are known for each input of CE-CT sequence. The weighted binary cross-entropy (BCE) loss is applied to the resection margin prediction task, while the negative log partial likelihood is used to predict the survival outcomes of a certain patient.

The determination module 504 is configured to determine whether the resection margin risk loss value and the survival risk loss value meet their respective loss thresholds.

A first risk loss threshold and a second risk loss threshold can be preset. The first risk loss threshold corresponds to the resection margin risk loss value. The second risk loss threshold corresponds to the survival risk loss value. When the resection margin risk loss value is less than or equal to the first risk loss threshold, it can be determined that the resection margin risk loss value meets the loss threshold. When the resection margin risk loss value is less than or equal to the second risk loss threshold, it can be determined that the resection margin risk loss value meets the loss threshold.

The training module 505, when the resection margin risk loss value and the survival risk loss value both meet their respective loss thresholds, is configured to stop the training of the first network structure and the second network structure to obtain a plurality of multi-task prediction models.

when both the resection margin risk loss value and the survival risk loss value fail to meet their respective loss thresholds, a plurality of training data sets is reacquired from the constructed data set, a plurality of multi-task prediction models being retained.

The selection module 506 is configured to select a target multi-task prediction model from the plurality of multi-task prediction models.

However many training data sets there are, there is a one-to-one correspondence between training data sets and multi-task prediction models.

In some embodiments, the selection module 506 selecting a target multi-task prediction model from the plurality of multi-task prediction models includes: obtaining a plurality of testing data sets from the constructed data set, each testing data set corresponding to each training data set; obtaining a plurality of testing values by using each testing data set to test the multi-task prediction model; determining a largest testing value among the plurality of testing values; and determining a multi-task prediction model corresponding to the largest testing value as the target multi-task prediction model.

A plurality of arrays are randomly obtained from the constructed data set each time to construct a training data set, and the remaining arrays in the data set can be used to construct a test data set. One test set can be used to test the corresponding multi-task prediction model to obtain the predicted value. The prediction value is used to indicate a prediction performance of the multi-task prediction model. The larger the prediction value, the better the prediction performance of the multi-task prediction model; otherwise, the smaller the prediction value, the worse the prediction performance of the multi-task prediction model. A target multi-task prediction model can be selected from the plurality of multi-task prediction models according to the testing values.

In some embodiments, the selection module 506 obtaining a plurality of testing values by using each testing data set to test the corresponding multi-task prediction model includes: calculating a mean value and a variance value of each training data set; standardizing each testing data set according to the mean value and the variance value of the corresponding testing data set; and obtaining the plurality of testing values by using each standardized testing data set to test the corresponding multi-task prediction model. By normalizing each enhanced medical image, a training efficiency of a joint learning model can be improved.

The prediction module 507 is configured to obtain a resection margin prediction value and a survival risk prediction value by predicting an enhanced medical image to be measured through the target multi-task prediction model.

The enhanced medical image to be measured can be an enhanced. CT image acquired by using the Computed Tomography to scan PDAC patients preparing for surgery.

To demonstrate the added value of the proposed signature to the current staging system, Kaplan-Meier survival curves are plotted, as in FIG. 4, for patients with further stratification by the signature after grouping by TNM and Tumor sizes respectively, these being two well-established stratification criteria. The cut-off for radiomics signature is the median score of each signature. Two subgroups of patients are studied: 1) patients divided by TNM staging I vs. II-III, and 2) patients divided by the primary PDAC tumor size≤20 mm vs. >20 mm. It is shown that the proposed signature remains the most significant log-rank test outcome in the subgroup of patients, while the radiomics signature does not reach the statistical significance within the patient subpopulation of PDAC tumor≤20 mm. Results shown in FIG. 3 demonstrate that after using the current clinicopathologic TNM staging system or tumor size, the proposed multi-phase CT imaging-based signature can indeed further provide the risk stratification with significant evidence. This novel deep signature can be combined with the established clinicopathological criteria to refine the risk stratification and guide the individualized treatment of PDAC patients.

The enhanced medical images processing device according to the present disclosure proposes a multi-task prediction model including a novel 3D Contrast-Enhanced Convolutional Long Short-Term Memory (CE-ConvLSTM) network to learn the enhancement dynamics of tumor attenuation from multi-phase CE-CT images. The multi-task prediction model can capture the tumor's temporal changes across several phases more effectively than the early fusion of input images. Furthermore, to allow the tumor resection margin information to contribute to the survival prediction preoperatively, the multi-task prediction model can be used to conduct a joint prediction of a resection margin prediction value and a survival risk prediction value. The joint learning of tumor significance and tumor attenuation in a multi-task setting can benefit both tasks and derive more effective/comprehensive prognosis-related deep image features. Extensive experimental results verify the effectiveness of the presented framework. The signature built from the proposed model remains strong in multivariable analysis adjusting for establishing clinical predictors and can be combined with the established criteria for risk stratification and management of PDAC patients.

Figure 6:
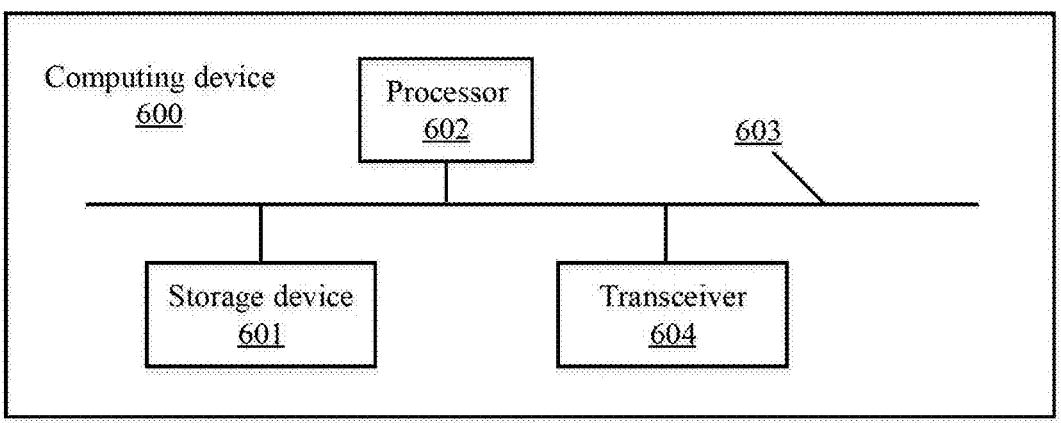
FIG. 6 shows a schematic structural diagram of a computing device applying the method according to the present disclosure.

FIG. 6 shows a schematic structural diagram of a computing device according to an embodiment of the present disclosure.

As shown in FIG. 6, the computing device 600 may include: at least one storage device 601, at least one processor 602, at least one communication bus 603, and a transceiver 604.

It should be understood by those skilled in the art that the structure of the computing device 600 shown in FIG. 6 does not constitute a limitation of the embodiment of the present disclosure. The computing device 600 may be a bus type structure or a star type structure, and the computing device 600 may also include more or less hardware or software than illustrated, or may have different component arrangements.

In at least one embodiment, the computing device 600 can include a terminal that is capable of automatically performing numerical calculations and/or information processing in accordance with pre-set or stored instructions. The hardware of the terminal can include, but is not limited to, a microprocessor, an application specific integrated circuit, programmable gate arrays, digital processors, and embedded devices. The computing device 600 may further include an electronic device. The electronic device can interact with a user through a keyboard, a mouse, a remote controller, a touch panel or a voice control device, for example, an individual computers, tablets, smartphones, digital cameras, etc.

It should be noted that the computing device 600 is merely an example, and other existing or future electronic products may be included in the scope of the present disclosure, and are included in the reference.

In some embodiments, the storage device 601 can be used to store program codes of computer readable programs and various data, such as the device for automatically delineating a clinical target volume of esophageal cancer 30 installed in the computing device 600, and automatically access to the programs or data with high speed during running of the computing device 600. The storage device 601 can include a read-only memory (ROM), a programmable read-only memory (PROM), an erasable programmable read only memory (EPROM), an one-time programmable read-only memory (OTPROM), an electronically-erasable programmable read-only memory (EEPROM), a compact disc read-only memory (CD-ROM), or other optical disk storage, magnetic disk storage, magnetic tape storage, or any other non-transitory storage medium readable by the computing device 600 that can be used to carry or store data.

In some embodiments, the at least one processor 602 may be composed of an integrated circuit, for example, may be composed of a single packaged integrated circuit, or may be composed of a plurality of integrated circuits of same function or different functions. The at least one processor 602 can include one or more central processing units (CPU), a microprocessor, a digital processing chip, a graphics processor, and various control chips. The at least one processor 602 is a control unit of the computing device 600, which connects various components of the computing device 600 using various interfaces and lines. By running or executing a computer program or modules stored in the storage device 601, and by invoking the data stored in the storage device 601, the at least one processor 602 can perform various functions of the computing device 600 and process data of the computing device 600.

In some embodiments, the least one bus 603 is used to achieve communication between the storage device 601 and the at least one processor 602, and other components of the compute device 600.

Although it is not shown, the computing device 600 may further include a power supply (such as a battery) for powering various components. In some embodiments, the power supply may be logically connected to the at least one processor 602 through a power management device, thereby, the power management device manages functions such as charging, discharging, and power management. The power supply may include one or more a DC or AC power source, a recharging device, a power failure detection circuit, a power converter or inverter, a power status indicator, and the like. The computing device 600 may further include various sensors, such as a BLUETOOTH module, a Wi-Fi module, and the like, and details are not described herein.

It should be understood that the described embodiments are for illustrative purposes only and are not limited by the scope of the present disclosure.

The above-described integrated unit implemented in a form of software function modules can be stored in a computer readable storage medium. The above software function modules are stored in a storage medium, and includes a plurality of instructions for causing a computing device (which may be a personal computer, or a network device, etc.) or a processor to execute the method according to various embodiments of the present disclosure.

In a further embodiment, in conjunction with FIG. 1, the at least one processor 602 can execute an operating device and various types of applications (such as the preoperative survival prediction device 50) installed in the computing device 600, program codes, and the like. For example, the at least one processor 602 can execute the modules 501-507.

In at least one embodiment, the storage device 601 stores program codes. The at least one processor 602 can invoke the program codes stored in the storage device 601 to perform related functions. For example, the modules described in FIG. 5 are program codes stored in the storage device 601 and executed by the at least one processor 602, to implement the functions of the various modules.

In at least one embodiment, the storage device 601 stores a plurality of instructions that are executed by the at least one processor 602 to implement all or part of the steps of the method described in the embodiments of the present disclosure.

Specifically, the storage device 601 stores the plurality of instructions which when executed by the at least one processor 602, causes the at least one processor 602 to: construct a data seta according to a plurality of enhanced medical images and a resection margin of each enhanced medical image, and obtain a plurality of training data sets from the constructed data set; for each training data set, input the training data set into a first network structure and a second network structure for training, extract first feature maps of the training data sets through the first network structure, and extract second feature maps of the training data sets through the second network structure; obtain joint feature maps by connecting the first feature maps and the second feature maps, obtain a resection margin risk loss value by calculating a resection margin risk loss function based on the joint feature maps, and obtain a survival risk loss value by calculating a survival risk loss function based on the joint feature maps; determine whether the resection margin risk loss value and the survival risk loss value meet their respective loss thresholds; when the resection margin risk loss value and the survival risk loss value both meet their respective loss thresholds, stop training the first network structure and the second network structure to obtain a plurality of multi-task prediction models; select a target multi-task prediction model from the plurality of multi-task prediction models; obtain a resection margin prediction value and a survival risk prediction value by predicting an enhanced medical image to be measured through the target multi-task prediction model.

The embodiment of the present disclosure further provides a computer storage medium, and the computer storage medium store a program that performs all or part of the steps including any of the method described in the above embodiments.

A non-transitory storage medium having stored thereon instructions that, when executed by a processor of a computing device, causes the computing device to perform an preoperative survival prediction method, the method including: constructing a data seta according to a plurality of enhanced medical images and a resection margin of each enhanced medical image, and obtaining a plurality of training data sets from the constructed data set; for each training data set, inputting the training data set into a first network structure and a second network structure for training, extracting first feature maps of the training data sets through the first network structure, and extracting second feature maps of the training data sets through the second network structure; obtaining joint feature maps by connecting the first feature maps and the second feature maps, obtaining a resection margin risk loss value by calculating a resection margin risk loss function based on the joint feature maps, and obtaining a survival risk loss value by calculating a survival risk loss function based on the joint feature maps; determining whether the resection margin risk loss value and the survival risk loss value meet their respective loss thresholds; when the resection margin risk loss value and the survival risk loss value both meet their respective loss thresholds, stop training the first network structure and the second network structure to obtain a plurality of multi-task prediction models; selecting a target multi-task prediction model from the plurality of multi-task prediction models; obtaining a resection margin prediction value and a survival risk prediction value by predicting an enhanced medical image to be measured through the target multi-task prediction model.

It should be noted that, for a simple description, the above method embodiments expressed as a series of action combinations, but those skilled in the art should understand that the present disclosure is not limited by the described action sequence. According to the present disclosure, some steps in the above embodiments can be performed in other sequences or simultaneously. Secondly, those skilled in the art should also understand that the embodiments described in the specification are all optional embodiments, and the actions and units involved are not necessarily required by the present disclosure.

In the above embodiments, descriptions of each embodiment has different focuses, and when there is no detail part in a certain embodiment, please refer to relevant parts of other embodiments.

In several embodiments provided in the preset application, it should be understood that the disclosed apparatus can be implemented in other ways. For example, the device embodiments described above are merely illustrative. For example, divisions of the unit are only a logical function division, and there can be other division ways in actual implementation.

The modules described as separate components may or may not be physically separated, and the components displayed as modules may or may not be physical units. That is, it can locate in one place, or distribute to a plurality of network units. Some or all of the modules can be selected according to actual needs to achieve the purpose of the solution of above embodiments.

In addition, each functional unit in each embodiment of the present disclosure can be integrated into one processing unit, or can be physically present separately in each unit, or two or more units can be integrated into one unit. The above integrated unit can be implemented in a form of hardware or in a form of a software functional unit.

It is apparent to those skilled in the art that the present disclosure is not limited to the details of the above-described exemplary embodiments, and the present disclosure can be embodied in other specific forms without departing from the spirit or essential characteristics of the present disclosure. Therefore, the present embodiments are to be considered as illustrative and not restrictive, and the scope of the present disclosure is defined by the appended claims instead all changes in the meaning and scope of equivalent elements are included in the present disclosure. Any reference signs in the claims should not be construed as limiting the claim.

The above embodiments are only used to illustrate technical solutions of the present disclosure, and are not restrictions on the technical solutions. Although the present disclosure has been described in detail with reference to the above embodiments, those skilled in the art should understand that the technical solutions described in one embodiments can be modified, or some of technical features can be equivalently substituted, and these modifications or substitutions do not detract from the essence of the technical solutions or from the scope of the technical solutions of the embodiments of the present disclosure.

We claim:

1. A preoperative survival prediction method based on enhanced medical images applicable in a computing device, the method comprising:
   constructing a data seta according to a plurality of enhanced medical images and a resection margin of each enhanced medical image, and obtaining a plurality of training data sets from the constructed data set;
   for each training data set, inputting the training data set into a first network structure and a second network structure for training, extracting first feature maps of the training data sets through the first network structure, and extracting second feature maps of the training data sets through the second network structure;
   obtaining joint feature maps by connecting the first feature maps and the second feature maps, obtaining a resection margin risk loss value by calculating a resection margin risk loss function based on the joint feature maps, and obtaining a survival risk loss value by calculating a survival risk loss function based on the joint feature maps;
   determining whether the resection margin risk loss value and the survival risk loss value meet their respective loss thresholds;
   when the resection margin risk loss value and the survival risk loss value both meet their respective loss thresholds, stopping the training of the first network structure and the second network structure, to obtain a plurality of multi-task prediction models;
   selecting a target multi-task prediction model from the plurality of multi-task prediction models;
   obtaining a resection margin prediction value and a survival risk prediction value by predicting an enhanced medical image to be measured through the target multi-task prediction model.

2. The preoperative survival prediction method of claim 1, wherein the method of constructing a data seta according to a plurality of enhanced medical images and a resection margin of each enhanced medical image comprises:
   obtaining a plurality of first target images by delineating a first target region in each enhanced medical image corresponding to a first phase;
   obtaining a plurality of second target images by segmenting a second target region in each enhanced medical image corresponding to a second phase;
   constructing an array by combining one enhanced medical image and the corresponding first target image, the corresponding second target image, and the corresponding resection margin, the data set including a plurality of the arrays.

3. The preoperative survival prediction method of claim 2, further comprising:
   defining a first threshold value and a second threshold value greater than the first threshold value;
   comparing each pixel value in the enhanced medical image with the first threshold value and comparing each pixel value in the enhanced medical image with the second threshold value;
   updating a pixel value according to the first threshold value, when the pixel value in the enhanced medical image is smaller than the first threshold value;
   updating a pixel value according to the second threshold value, when the pixel value in the enhanced medical image is greater than the second threshold value;
   keeping a pixel value unchanged, when the pixel value in the enhanced medical image is greater than the first threshold but less than the second threshold;
   updating the enhanced medical image according to the updated pixel value.

4. The preoperative survival prediction method of claim 3, wherein the method of selecting a target multi-task prediction model from the plurality of multi-task prediction models comprises:
   obtaining a plurality of testing data sets from the constructed data set, each testing data set corresponding to each training data set;
   obtaining a plurality of testing values by using each testing data set to test the corresponding multi-task prediction model;

determining a largest testing value among the plurality of testing values; and determining a multi-task prediction model corresponding to the largest testing value as the target multi-task prediction model.

5. The preoperative survival prediction method of claim 4, wherein the method of obtaining a plurality of testing values by using each testing data set to test the corresponding multi-task prediction model comprises:

calculating a mean value and a variance value of each training data set;

standardizing each testing data set according to the mean value and the variance value of the corresponding testing data set; and obtaining the plurality of testing values by using each standardized testing data set to test the corresponding multi-task prediction model.

6. The preoperative survival prediction method of claim 5, further comprising:

obtaining a plurality of resampled enhanced medical images by resampling each enhanced medical image into an isotropic enhanced medical image; and enhancing the plurality of resampled enhanced medical images, comprising rotating the plurality of resampled enhanced medical images according to a pre-rotation angle; or randomly zooming the plurality of resampled enhanced medical images.

7. The preoperative survival prediction method of claim 5, wherein the first network structure being a 3D-CNN model with six convolutional layers equipped with batch normalization and relu, the second network structure being a CE-ConvLSTM model with a Res Tet model cascaded before, the resection margin risk loss function being a binary cross-entropy loss function, and the survival risk loss function being $L(y_i)=\Sigma_i \delta_i(-y_i+\log \Sigma_{j:t_j \geq t_i} \exp(y_j))$, where j is from the set whose survival time is equal or larger than $t_i$ ($t_j \geq t_i$).

8. A computing device, comprising:

at least one processor; and a storage device storing one or more programs which when executed by the at least one processor, causes the at least one processor to:

construct a data seta according to a plurality of enhanced medical images and a resection margin of each enhanced medical image, and obtain a plurality of training data sets from the constructed data set;

for each training data set, input the training data set into a first network structure and a second network structure for training, extract first feature maps of the training data sets through the first network structure, and extract second feature maps of the training data sets through the second network structure;

obtain joint feature maps by connecting the first feature maps and the second feature maps, obtain a resection margin risk loss value by calculating a resection margin risk loss function based on the joint feature maps, and obtain a survival risk loss value by calculating a survival risk loss function based on the joint feature maps;

determine whether the resection margin risk loss value and the survival risk loss value meet their respective loss thresholds;

when the resection margin risk loss value and the survival risk loss value both meet their respective loss thresholds, stop the training of the first network structure and the second network structure, to obtain a plurality of multi-task prediction models;

select a target multi-task prediction model from the plurality of multi-task prediction models;

obtain a resection margin prediction value and a survival risk prediction value by predicting an enhanced medical image to be measured through the target multi-task prediction model.

9. The computing device of claim 8, wherein the method of constructing a data seta according to a plurality of enhanced medical images and a resection margin of each enhanced medical image comprises:

obtaining a plurality of first target images by delineating a first target region in each enhanced medical image corresponding to a first phase;

obtaining a plurality of second target images by segmenting a second target region in each enhanced medical image corresponding to a second phase;

constructing an array by combining one enhanced medical image and the corresponding first target image, the corresponding second target image, and the corresponding resection margin, the data set including a plurality of the arrays.

10. The computing device of claim 9, the at least one processor further to:

define a first threshold value and a second threshold value greater than the first threshold value;

compare each pixel value in the enhanced medical image with the first threshold value and comparing each pixel value in the enhanced medical image with the second threshold value;

update a pixel value according to the first threshold value, when the pixel value in the enhanced medical image is smaller than the first threshold value;

update a pixel value according to the second threshold value, when the pixel value in the enhanced medical image is greater than the second threshold value;

keep a pixel value unchanged, when the pixel value in the enhanced medical image is greater than the first threshold but less than the second threshold;

update the enhanced medical image according to the updated pixel value.

11. The computing device of claim 10, wherein the method of selecting a target multi-task prediction model from the plurality of multi-task prediction models comprises:

obtaining a plurality of testing data sets from the constructed data set, each testing data set corresponding to each training data set;

obtaining a plurality of testing values by using each testing data set to test the corresponding multi-task prediction model;

determining a largest testing value among the plurality of testing values; and determining a multi-task prediction model corresponding to the largest testing value as the target multi-task prediction model.

12. The computing device of claim 11, wherein the method of obtaining a plurality of testing values by using each testing data set to test the corresponding multi-task prediction model comprises:

calculating a mean value and a variance value of each training data set;

standardizing each testing data set according to the mean value and the variance value of the corresponding testing data set; and obtaining the plurality of testing values by using each standardized testing data set to test the corresponding multi-task prediction model.

13. The computing device of claim 12, the at least one processor further to:
obtain a plurality of resampled enhanced medical images by resampling each enhanced medical image into an isotropic enhanced medical image; and
enhance the plurality of resampled enhanced medical images, comprising rotating the plurality of resampled enhanced medical images according to a pre-rotation angle; or randomly zooming the plurality of resampled enhanced medical images.

14. The computing device of claim 12, wherein the first network structure being a 3D-CNN model with six convolutional layers equipped with batch normalization and relu, the second network structure being a CE-ConvLSTM model with a ResNet model cascaded before, the resection margin risk loss function being a binary cross-entropy loss function, and the survival risk loss function being $L(y_i)=\Sigma_i \delta_i(-y_i+\log \Sigma_{j:t_j \geq t_i} \exp(y_j))$, where j is from the set whose survival time is equal or larger than $t_i$ ($t_j \geq t_i$).

15. A non-transitory storage medium having stored thereon instructions that, when executed by a processor of a computing device, causes the computing device to perform a preoperative survival prediction method based on enhanced medical images, the method comprising:
constructing a data seta according to a plurality of enhanced medical images and a resection margin of each enhanced medical image, and obtaining a plurality of training data sets from the constructed data set;
for each training data set, inputting the training data set into a first network structure and a second network structure for training, extracting first feature maps of the training data sets through the first network structure, and extracting second feature maps of the training data sets through the second network structure;
obtaining joint feature maps by connecting the first feature maps and the second feature maps, obtaining a resection margin risk loss value by calculating a resection margin risk loss function based on the joint feature maps, and obtaining a survival risk loss value by calculating a survival risk loss function based on the joint feature maps;
determining whether the resection margin risk loss value and the survival risk loss value meet their respective loss thresholds;
when the resection margin risk loss value and the survival risk loss value both meet their respective loss thresholds, stopping the training of the first network structure and the second network structure to obtain a plurality of multi-task prediction models;
selecting a target multi-task prediction model from the plurality of multi-task prediction models;
obtaining a resection margin prediction value and a survival risk prediction value by predicting an enhanced medical image to be measured through the target multi-task prediction model.

16. The non-transitory storage medium of claim 15, wherein the method of constructing a data seta according to a plurality of enhanced medical images and a resection margin of each enhanced medical image comprises:
obtaining a plurality of first target images by delineating a first target region in each enhanced medical image corresponding to a first phase;
obtaining a plurality of second target images by segmenting a second target region in each enhanced medical image corresponding to a second phase;
constructing an array by combining one enhanced medical image and the corresponding first target image, the corresponding second target image, and the corresponding resection margin, the data set including a plurality of the arrays.

17. The non-transitory storage medium of claim 16, further comprising:
defining a first threshold value and a second threshold value greater than the first threshold value;
comparing each pixel value in the enhanced medical image with the first threshold value and comparing each pixel value in the enhanced medical image with the second threshold value;
updating a pixel value according to the first threshold value, when the pixel value in the enhanced medical image is smaller than the first threshold value;
updating a pixel value according to the second threshold value, when the pixel value in the enhanced medical image is greater than the second threshold value;
keeping a pixel value unchanged, when the pixel value in the enhanced medical image is greater than the first threshold but less than the second threshold;
updating the enhanced medical image according to the updated pixel value.

18. The non-transitory storage medium of claim 17, wherein the method of selecting a target multi-task prediction model from the plurality of multi-task prediction models comprises:
obtaining a plurality of testing data sets from the constructed data set, each testing data set corresponding to each training data set;
obtaining a plurality of testing values by using each testing data set to test the corresponding multi-task prediction model;
determining a largest testing value among the plurality of testing values; and
determining a multi-task prediction model corresponding to the largest testing value as the target multi-task prediction model.

19. The non-transitory storage medium of claim 18, wherein the method of obtaining a plurality of testing values by using each testing data set to test the corresponding multi-task prediction model comprises:
calculating a mean value and a variance value of each training data set;
standardizing each testing data set according to the mean value and the variance value of the corresponding testing data set; and
obtaining the plurality of testing values by using each standardized testing data set to test the corresponding multi-task prediction model.

20. The non-transitory storage medium of claim 18, further comprising:
obtaining a plurality of resampled enhanced medical images by resampling each enhanced medical image into an isotropic enhanced medical image; and
enhancing the plurality of resampled enhanced medical images, comprising rotating the plurality of resampled enhanced medical images according to a pre-rotation angle; or randomly zooming the plurality of resampled enhanced medical images.

* * * * *